(12) United States Patent
Varona et al.

(10) Patent No.: US 6,673,980 B1
(45) Date of Patent: Jan. 6, 2004

(54) ABSORBENT PRODUCT WITH CREPED NONWOVEN DAMPNESS INHIBITOR

(75) Inventors: Eugenio Go Varona, Marietta, GA (US); Carol Ann Blaney, Roswell, GA (US); Audrie Tomoko Ono, Atlanta, GA (US); Tamara Lee Mace, Doraville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/345,359

(22) Filed: Jul. 16, 1999

(51) Int. Cl.[7] .............................................. A61F 13/20
(52) U.S. Cl. ..................... 604/367; 604/365; 604/366; 604/370
(58) Field of Search ................................ 604/367, 385.1, 604/361, 385.23, 378, 370, 365, 366; 428/105, 107, 112, 152, 340, 198; 442/409

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,502,538 A | 3/1970 | Petersen | 161/150 |
| 3,502,763 A | 3/1970 | Hartmann | 264/210 |
| 3,542,615 A | 11/1970 | Dobo et al | 156/181 |
| 3,692,618 A | 9/1972 | Dorschner et al. | 161/72 |
| 3,695,269 A * | 10/1972 | Malaney | 128/284 |
| 3,802,817 A | 4/1974 | Matsuki et al. | 425/66 |
| 3,849,241 A | 11/1974 | Butin et al. | 161/169 |
| 3,901,236 A | 8/1975 | Assarsson et al. | 128/284 |
| 3,927,673 A | 12/1975 | Taylor | 128/287 |
| 3,949,128 A | 4/1976 | Ostermeier | 428/152 |
| 4,041,203 A | 8/1977 | Brock et al. | 428/157 |
| 4,076,663 A | 2/1978 | Masuda et al. | 260/17.4 GC |
| 4,282,874 A | 8/1981 | Mesek | 128/287 |
| 4,284,594 A | 8/1981 | Job et al. | 264/41 |
| 4,286,082 A | 8/1981 | Tsubakimoto et al. | 526/240 |
| 4,288,494 A | 9/1981 | Porter et al. | 428/398 |
| 4,306,559 A | 12/1981 | Nishizawa et al. | 128/287 |
| 4,308,303 A | 12/1981 | Mastroianni et al. | 428/90 |
| 4,340,563 A | 7/1982 | Appel et al. | 264/518 |
| 4,394,930 A | 7/1983 | Korpman | 220/444 |
| 4,655,760 A | 4/1987 | Morman et al. | 604/385 |
| 4,663,220 A | 5/1987 | Wisneski et al. | 428/221 |
| 4,676,785 A | 6/1987 | Battista | 604/369 |
| 4,681,578 A | 7/1987 | Anderson et al. | 604/385 |
| 4,681,793 A | 7/1987 | Linman et al. | 428/138 |
| 4,704,116 A | 11/1987 | Enloe | 604/385 A |
| 4,758,239 A | 7/1988 | Yeo et al. | 604/366 |
| 4,777,073 A | 10/1988 | Sheth | 428/155 |
| 4,818,600 A | 4/1989 | Braun et al. | 428/290 |
| 4,940,464 A | 7/1990 | Van Gompel et al. | 604/396 |
| 5,043,209 A | 8/1991 | Boissé et al. | 428/233 |
| 5,046,272 A | 9/1991 | Vogt et al. | 38/143 |
| 5,104,116 A | 4/1992 | Pohjola | 271/185 |
| 5,190,533 A | 3/1993 | Blackburn | 604/367 |

(List continued on next page.)

FOREIGN PATENT DOCUMENTS

| | | | |
|---|---|---|---|
| EP | 217 032 | 4/1987 | D04H/13/00 |
| EP | 0 813 848 A1 | 12/1997 | A61F/13/15 |
| EP | 887 054 | 12/1998 | A61F/13/15 |
| EP | 0 893 113 A1 | 1/1999 | A61F/13/15 |
| EP | 0 953 324 | 11/1999 | A61F/13/15 |

(List continued on next page.)

*Primary Examiner*—Weilun Lo
*Assistant Examiner*—Michele Kidwell
(74) *Attorney, Agent, or Firm*—Pauley Petersen & Erickson

(57) ABSTRACT

An absorbent article including a liquid-permeable top layer, an absorbent core layer, a breathable outer cover, and a creped inner nonwoven fibrous layer between the absorbent core and breathable outer cover. The creped inner nonwoven fibrous layer has a level of creping of about 5–75%, and is preferably permanently creped. The creped inner nonwoven fibrous layer serves as a dampness inhibitor which reduces or prevents perceived dampness on the external surface of the outer cover by lowering thermal conductivity between the absorbent core and the outer cover surface.

43 Claims, 6 Drawing Sheets

U.S. PATENT DOCUMENTS

| | | | |
|---|---|---|---|
| 5,224,405 A | 7/1993 | Pohjola | 83/24 |
| 5,226,992 A | 7/1993 | Morman | 156/62.4 |
| 5,272,236 A | 12/1993 | Lai et al. | 526/348.5 |
| 5,294,478 A | 3/1994 | Wanek et al. | 428/218 |
| 5,300,054 A | 4/1994 | Feist et al. | 604/378 |
| 5,304,161 A | 4/1994 | Noel et al. | 604/378 |
| 5,322,728 A | 6/1994 | Davey et al. | 428/296 |
| 5,344,698 A | 9/1994 | Rock et al. | 428/253 |
| 5,346,487 A | 9/1994 | Lovestedt | 604/385.1 |
| 5,387,209 A | 2/1995 | Yamamoto et al. | 604/384 |
| 5,401,267 A | 3/1995 | Couture-Dorschner et al. | 604/384 |
| 5,437,653 A | 8/1995 | Gilman et al. | 604/378 |
| 5,439,458 A | 8/1995 | Noel et al. | 604/378 |
| 5,439,626 A | 8/1995 | Bennett et al. | 264/103 |
| 5,460,622 A | 10/1995 | Dragoo et al. | 604/378 |
| 5,466,513 A | 11/1995 | Wanek et al. | 428/218 |
| 5,527,303 A | 6/1996 | Milby, Jr. et al. | 604/385.1 |
| 5,558,658 A | 9/1996 | Menard et al. | 604/385.1 |
| 5,569,233 A | 10/1996 | Goulait | 604/391 |
| 5,571,096 A | 11/1996 | Dobrin et al. | 604/383 |
| 5,571,619 A | 11/1996 | McAlpin et al. | 428/364 |
| 5,591,297 A | 1/1997 | Ahr | 156/521 |
| 5,603,707 A | 2/1997 | Trombetta et al. | 604/383 |
| 5,626,571 A * | 5/1997 | Young et al. | 604/370 |
| 5,643,239 A | 7/1997 | Bodford et al. | 604/370 |
| 5,653,699 A | 8/1997 | Reed et al. | 604/307 |
| 5,656,372 A | 8/1997 | Gentile et al. | 428/376 |
| 5,680,653 A | 10/1997 | Mathis et al. | 2/123 |
| 5,695,868 A * | 12/1997 | McCormack | 428/283 |
| 5,788,684 A | 8/1998 | Abuto et al. | 604/368 |
| 5,810,797 A | 9/1998 | Menard et al. | 604/378 |
| 5,817,081 A | 10/1998 | LaVon et al. | 604/378 |
| 5,843,056 A * | 12/1998 | Good et al. | 604/367 |
| 5,843,057 A * | 12/1998 | McCormack | 604/367 |
| 5,843,066 A | 12/1998 | Dobrin | 604/385.1 |
| 5,873,963 A | 2/1999 | Trombetta et al. | 156/622 |
| 5,879,341 A | 3/1999 | Odorzynski et al. | 604/367 |
| 5,897,541 A | 4/1999 | Uitenbroek et al. | 604/358 |
| 5,914,184 A | 6/1999 | Morman | 428/315.9 |
| 5,928,209 A | 7/1999 | Bodford et al. | 604/370 |
| 5,932,316 A | 8/1999 | Cree et al. | 428/182 |
| 5,955,187 A | 9/1999 | McCormack et al. | 428/315.5 |
| 5,990,377 A * | 11/1999 | Chen et al. | 604/381 |
| 6,037,281 A | 3/2000 | Mathis et al. | 442/394 |
| 6,045,900 A | 4/2000 | Haffner | 428/315.9 |
| 6,072,005 A | 6/2000 | Kobylivker et al. | 525/240 |
| 6,152,906 A | 11/2000 | Faulks et al. | 604/385.01 |
| 6,177,607 B1 | 1/2001 | Blaney et al. | 604/378 |
| 6,197,404 B1 * | 3/2001 | Varona | 428/152 |
| 6,369,292 B1 | 4/2002 | Strack et al. | 604/370 |

FOREIGN PATENT DOCUMENTS

| | | | |
|---|---|---|---|
| EP | 1 051 958 A1 | 11/2000 | |
| GB | 2 029 764 A | 7/1979 | |
| GB | 2 296 216 A | 6/1996 | |
| JP | 08164160 | 6/1996 | |
| JP | 02846448 | 1/1999 | |
| WO | WO 94/14394 | 7/1994 | |
| WO | WO 95/16422 | 6/1995 | |
| WO | 96/09165 | 3/1996 | B32B/27/12 |
| WO | 96/19346 | 6/1996 | B32B/7/00 |
| WO | 96/21409 | 7/1996 | A61F/13/00 |
| WO | WO 96/39109 | 12/1996 | A61F/13/15 |
| WO | 97/16148 | 5/1997 | A61F/13/15 |
| WO | 97/24095 | 7/1997 | A61F/13/15 |
| WO | 97/24097 | 7/1997 | A61F/13/15 |
| WO | 97/34557 | 9/1997 | A61F/13/15 |
| WO | 97/36561 | 10/1997 | A61F/13/15 |
| WO | 97/36562 | 10/1997 | A61F/13/15 |
| WO | WO 97/45259 | 12/1997 | B32B/27/12 |
| WO | WO 98/24621 | 6/1998 | |
| WO | 98/27920 | 7/1998 | A61F/13/15 |
| WO | 98/29480 | 7/1998 | C08J/5/18 |
| WO | 99/16400 | 4/1999 | A61F/13/15 |
| WO | WO 99/22619 | 5/1999 | A44B/18/00 |
| WO | WO 99/25283 | 5/1999 | A61F/13/15 |
| WO | 99/32288 | 7/1999 | B32B/27/12 |
| WO | WO 99/55265 | 11/1999 | |
| WO | 00/10497 | 3/2000 | A61F/13/15 |

* cited by examiner

ABSORBENT PRODUCT WITH CREPED NONWOVEN DAMPNESS INHIBITOR

FIELD OF THE INVENTION

The present invention is directed to an absorbent product having at least a top layer, an absorbent core, and a breathable outer cover material. A fibrous nonwoven web having creped regions is disposed between the absorbent core and the breathable outer cover, causing a reduction in surface dampness on the outer surface of the breathable outer cover material when the absorbent core is wet without significantly reducing breathability of the outer cover when the absorbent core is dry.

BACKGROUND OF THE INVENTION

Absorbent articles, such as diapers, child training pants, adult incontinence garments, swim wear and the like, typically include at least a liquid-permeable top layer for direct contact with the wearer, an absorbent core layer, and a substantially liquid-impermeable outer cover material. The absorbent core is positioned between the top layer and the outer cover material. When the absorbent article is exposed to a liquid insult, liquid passes through the top layer and into the absorbent core. The outer cover prevents the liquid in the absorbent core from leaving the garment.

Many of today's absorbent garments utilize breathable outer cover materials. Breathable outer cover materials are substantially impermeable to liquids, but are permeable to water vapor. Breathable outer cover materials permit escape of water vapor from the absorbent garment, increasing the garment comfort and reducing skin rashes and other irritations that result when water vapor is trapped inside the garment and heated by the wearer's body. Many of today's absorbent garments are highly breathable, for maximum wearer comfort.

One shortcoming of breathable absorbent articles is a cold, damp, clammy feel that often occurs on the outside of the garment, i.e., on the outside of the outer cover material. This perceived surface dampness is caused when liquid water vaporizes from the absorbent core and passes through the microporous outer cover, removing heat from the diaper's absorbent core via evaporative cooling. This in turn leaves the outer cover surface feeling cold and clammy, which is perceived by the consumer as damp. There is a need or desire in the absorbent garment industry for absorbent articles which are highly breathable, yet which reduce or avoid the perceived dampness caused by evaporative cooling.

SUMMARY OF THE INVENTION

The present invention is directed to an absorbent article having a breathable outer cover material and reduced perceived outer cover dampness. The absorbent article includes at least a liquid-permeable top layer, a breathable, substantially liquid impermeable outer cover material, and an absorbent core layer between the top layer and the outer cover material. The outer cover material may include a breathable film laminated to a nonwoven filament web, and may be positioned with the film facing inward (i.e., toward the absorbent core) and with the nonwoven web facing outward. In accordance with the invention, a second nonwoven filament web is interposed between the absorbent core and the breathable outer cover material. The second nonwoven web comprises a creped thermoplastic nonwoven web.

Preferably, the creped nonwoven web has interfilament bonded areas which are bent or oriented permanently out-of-plane, unbonded areas between the bonded areas, and filament looping in the unbonded areas. Preferably, at least some of the filaments have hollow interiors.

The creped thermoplastic nonwoven web has a three-dimensional structure which traps a quantity or layer of air between the absorbent core and the outer cover. The air layer, partially encapsulated in the creped nonwoven web, insulates and slows heat transfer between the absorbent core and the outer cover. The evaporative cooling from a wet absorbent core is less readily transmitted to the outer cover, causing the outer surface of the outer cover to feel warmer and drier when touched.

Furthermore, the creped nonwoven layer provides paths for sideways diffusion and convection, facilitating the removal of moisture from the diaper, including moisture near the skin. This contributes to reduced skin hydration. Furthermore, the creped nonwoven layer, and the air within it, causes the diaper to have a resilient, soft, springy surface feel. Finally, the creped nonwoven filament web is permeable enough so as not to appreciably reduce moisture vapor transmission from the absorbent core through the outer cover material.

The creped thermoplastic nonwoven web may be composed wholly or partially of hollow thermoplastic filaments. The hollow filaments trap additional air, thereby increasing the insulative properties. Also, the hollow filaments lower the overall material cost and facilitate bulk and rigidity in the creped thermoplastic nonwoven web.

With the foregoing in mind, it is a feature and advantage of the invention to provide an absorbent article with a breathable outer cover system whose thermal conductivity is favorably decreased by the addition of a creped nonwoven web between the outer cover and absorbent core.

It is also a feature and advantage of the invention to provide a breathable absorbent article having a dampness-inhibiting layer which does not appreciably reduce breathability of the outer cover.

It is also a feature and advantage of the invention to provide an absorbent article having a breathable outer cover which remains warm and dry to the touch under a wide variety of conditions.

It is also a feature and advantage of the invention to provide an absorbent article having a resilient, soft, springy surface feel.

The foregoing and other features and advantages will become further apparent from the following detailed description of the presently preferred embodiments, read in conjunction with the accompanying examples and drawings. The detailed description, examples and drawing are intended to be illustrative rather than limiting, the scope of the invention being defined by the appended claims and equivalents thereof.

DEFINITIONS

Figure 1:
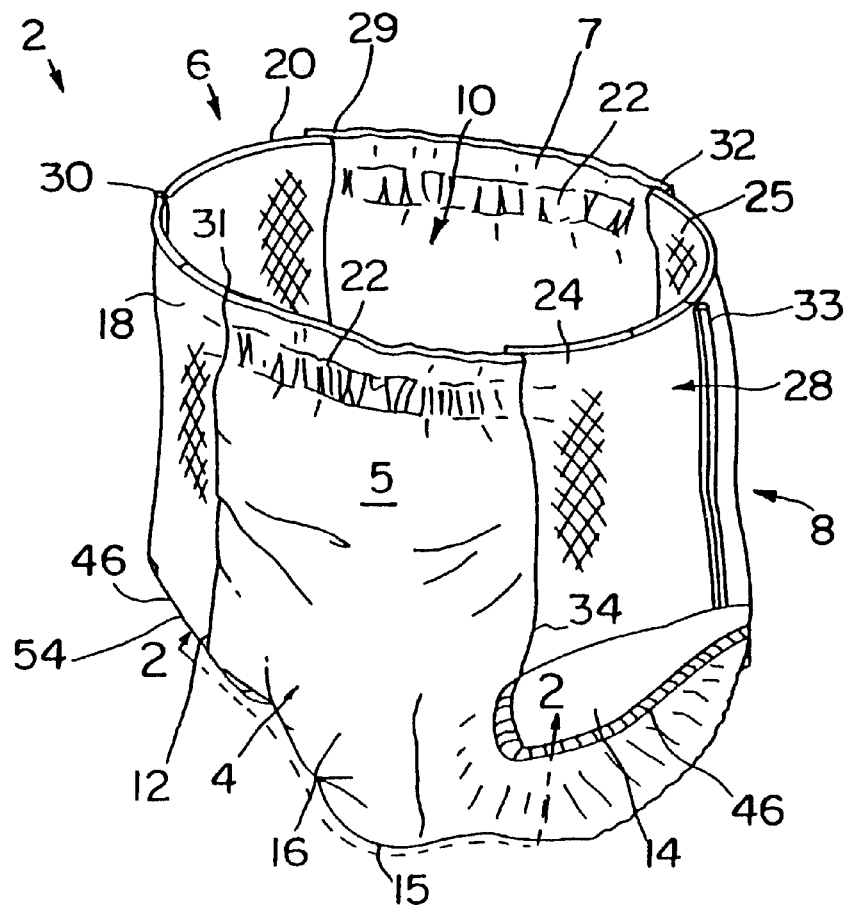
FIG. 1 is a perspective view of an absorbent article of the invention.

The terms "breathable film," "breathable laminate" or "breathable outer cover material" refer to a film, laminate, or outer cover material having a water vapor transmission rate ("WVTR") of at least about 300 grams/m²–24 hours, using the WVTR Test Procedure described herein.

The term "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers typically having an average fiber denier of about 0.005–10, for example, having an average fiber denier of about 0.05–6, or more particularly, microfibers may have an average fiber denier of about 1–4.

The term "denier" is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15_2 \times 0.89 \times 0.00707 = 1.415$). Outside the United States the unit of measurement is more commonly the "tex," which is defined as the grams per kilometer of fiber. Tex may be calculated as denier/9. The "mean fiber denier" is the sum of the deniers for each fiber, divided by the number of fibers.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3 microns, more particularly, between about 0.6 and 10.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

The term "film" refers to a thermoplastic film made using a film extrusion process, such as a cast film or blown film extrusion process. The term "water-permeable porous films" refers to films rendered porous by puncturing or aperturing, and to films rendered porous by mixing polymer with filler, forming a film from the mixture, and stretching the film.

The term "polymer" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

The term "superabsorbent material" refers to a water-swellable, water-insoluble organic or inorganic material capable, under the most favorable conditions, of absorbing at least about 20 times its weight, preferably at least about 30 times its weight in an aqueous solution containing 0.9% by weight sodium chloride.

The term "personal care absorbent product" includes without limitation diapers, training pants, swim wear, absorbent underpants, baby wipes, adult incontinence products, and feminine hygiene products.

The term "medical absorbent product" includes without limitation absorbent garments, underpads, bandages, absorbent drapes, and medical wipes.

"Creped" refers to a nonwoven web having portions which are bent out-of-plane using a variety of creping techniques known in the art. Creped nonwoven webs have top and/or bottom surfaces which define a three-dimensional structure. The three-dimensional structure is manifested in the form of puckering, waves, peaks and valleys, etc., so that some regions of the nonwoven web are substantially elevated or depressed relative to adjacent regions.

"Permanently creped" refers to a creped nonwoven web having bonded and unbonded areas, in which the bonded areas are permanently bent out-of-plane and the unbonded portions are permanently looped, such that the nonwoven web cannot be returned to its original uncreped state by applying a mechanical stress.

"Crepe level" is a measure of creping and is calculated according to the following equation:

$$\text{Crepe level } (\%) = \frac{\text{Speed of Creping Surface minus speed of windup reel for the creped web}}{\text{Speed of Creping Surface}} \times 100$$

"Bent out-of-plane" refers to a bonding or orientation of portions of the nonwoven web in a direction away from the plane in which the nonwoven web substantially lies before being subjected to the creping process. As used herein, the phrase "bent out-of-plane" generally refers to nonwoven webs having creped portions bent at least about 15 degrees away from the plane of the uncreped nonwoven web, preferably at least about 30 degrees.

"Looped" refers to unbonded filaments or portions of filaments in a creped nonwoven web which define an arch, semi-circle or similar configuration extending above the plane of the uncreped nonwoven web, and terminating at both ends in the nonwoven web (e.g., in the bonded areas of the creped nonwoven web).

"Nonwoven web bond pattern" is a pattern of interfilament bonding in the nonwoven web which is imparted during manufacture of the nonwoven web.

"Hydrophobic" refers to a surface or material that is poorly wetted by water, has little or no affinity for water, and tends to repel water. Hydrophobic surfaces generally have a water contact angle of 90 degrees or greater, when treated with droplets of water.

"Hydrophilic" refers to a surface or material that has an affinity for water, and is wettable by water. Hydrophilic surfaces generally have a water contact angle of less than 90 degrees, when treated with droplets of water.

DETAILED DESCRIPTION OF THE PRESENTLY PREFERRED EMBODIMENTS

Referring to FIG. 1 of the drawings, an absorbent garment 2 of the invention has a pant-like configuration useful for diapers, child training pants, child swim wear, adult incontinence articles, and the like. The garment 2 includes a waste containment section ("chassis") 4 having front portion 5 and rear portion 7 joined by central ("crotch") portion 15, and two side portions 6 and 8, each of which is connected at its edges to the front and rear portions. The side panel 6 includes stretchable panels 18 and 20 joined to each other along seam 30, and joined to the waste containment section along seams 29 and 31. Each of the seams 29, 30 and 31 is longitudinally oriented, and extends from the top of the waist opening 10 to the leg opening 12. The side panel 8 includes stretchable panels 24 and 26 joined to each other along seam 33, and joined to the waste containment section along seams 32 and 34. Each of the seams 32, 33 and 34 is longitudinally oriented, and extends from the top of the waist opening to the leg opening 14.

Chassis 4 includes multiple layers (described below) including, for instance, a liquid-permeable top layer, an absorbent core layer, and a breathable liquid-impermeable outer cover layer 16 which faces away from the wearer. An inner nonwoven filament web, positioned between the absorbent core and outer cover 16, is described below. The waste containment section 4 also includes elasticized waist portions 22 on the front and back of the garment. The leg opening portions 12 and 14 also include elastic portions 46 which extend substantially around the portion of the leg openings defined by the waste containment section 4.

Figure 2:
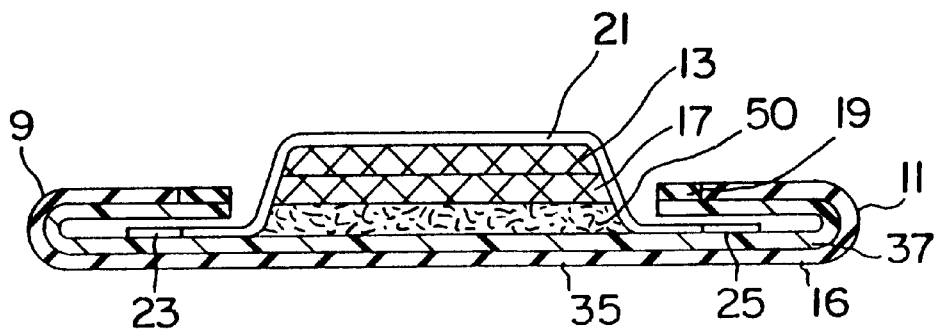
FIG. 2 is an expanded sectional view of the absorbent article of the invention, taken along the line 2—2 in FIG. 1.

FIG. 2 shows an expanded cutout view of the individual layers of the absorbent article, taken along the line 2—2 in FIG. 1. Referring to FIG. 2, the absorbent garment 2 includes several layers in the central region 15. The layers include a liquid-permeable top layer 21, a liquid-permeable surge layer 13 adjacent and below the top layer 21, an absorbent layer 17 adjacent and below the surge layer 13, an inner nonwoven filament web 50 adjacent and below the absorbent layer 17, and a breathable, substantially liquid impermeable outer cover 16 adjacent and below the inner nonwoven filament web 50.

In the embodiment shown, the top layer 21 and outer cover material 16 are wider than surge layer 13, absorbent core 17, and inner web 50. The top layer 21 substantially surrounds the surge layer 13, absorbent core 17, and inner nonwoven filament web 50, and is affixed at end regions 23 and 25 to the outer cover material 16 using an adhesive, ultrasonic or thermal bonding technique. The outer cover material 16 is folded over at both lateral ends 9 and 11, so that it overlaps and envelops the edges 23 and 25 of the top layer 21. Within the overlap, the layers can be bonded together using thermal, ultrasonic, or adhesive bonding. The elastic regions 46 can be formed with elastic bands 19 affixed to, and/or within, the outer cover material 16 using an adhesive, ultrasonic, or thermal bonding technique.

The longitudinal seams 29–34 may be formed by conventional methods including, without limitation, ultrasonic welding, thermal bonding, adhesive bonding, stitch bonding and the like. Ultrasonic welding is a presently preferred technique. The various bonding techniques are conventional, and are neither critical nor limiting as to the present invention.

The stretchable side panels 6 and 8 can be constructed of conventional woven or nonwoven materials, formed from a wide variety of elastic and stretchable polymers. The terms "elastic" and "stretchable" include any material which can be stretched, and which tends to return to its original shape when relaxed. Suitable polymers include without limitation block copolymers of polystyrene, polyisoprene and polybutadiene; copolymers of ethylene, natural rubbers and urethanes; and combinations of the foregoing. Particularly suitable are styrene-butadiene block copolymers sold by Shell Chemical Co. under the trade name KRATON®. Other suitable polymers include copolymers of ethylene, including without limitation ethylene vinyl acetate, ethylene methyl acrylate, ethylene ethyl acrylate, ethylene acrylic acid, stretchable ethylene-propylene copolymers, and combinations thereof. Also suitable are coextruded composites of the foregoing, and elastomeric staple integrated composites where staple fibers of polypropylene, polyester, cotton and other materials are integrated into an elastomeric meltblown web. Certain elastomeric single-site or metallocene-catalyzed olefin polymers and copolymers are also suitable for the side panels. The stretchable side panels are preferably rectangular in shape, and preferably extend from the top of the waist opening 10 to the leg openings 12 and 14. The side panels may also be laminates of multiple layers, and are preferably breathable to water vapor but impervious to liquids.

Both the surge layer 13 and body side liner 21 are constructed from highly liquid pervious materials. These layers function to transfer liquid from the wearer to the absorbent layer 17. Suitable materials include porous woven materials, porous nonwoven materials, and apertured films. Examples include, without limitation, any flexible porous sheets of polyolefin fibers, such as polypropylene, polyethylene or polyester fibers; webs of spunbonded polypropylene, polyethylene or polyester fibers; webs of rayon fibers; bonded carded webs of synthetic or natural fibers or combinations thereof. Either layer may also be an apertured plastic film.

The various layers of garment 2 have dimensions which vary depending on the size and shape of the wearer.

Absorbent layer 17 can be made of wood pulp fluff or a mixture of wood pulp fluff and a superabsorbent material, or a wood pulp fluff integrated with a thermoplastic absorbent material treated with a surfactant. Thermal binders, such as Pulpex® can be used in blends or layering with the fluff and superabsorbent. Layer 17 can also be a batt of meltblown synthetic fibers, a bonded carded web of synthetic or natural fibers or blends thereof, a composite of meltblown fibers and the like. The synthetic fibers can be, but are not limited to, polypropylene, polyethylene, polyester and copolymers of these or other polyolefins.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

The outer cover material 16 is breathable to water vapor. Generally the outer cover 16 will have a WVTR of at least about 300 grams/m$^2$–24 hours using the test procedure described below, preferably at least about 1500 grams/m$^2$–24 hours, more preferably at least about 3000 grams/m$^2$–24 hours. Outer cover 16 shown in FIG. 2 includes two layers 35 and 37, joined by thermal or ultrasonic bonding, or an adhesive. Layer 35 is a nonwoven filament web. Layer 37 is a breathable film. Outer cover 16 is positioned with nonwoven web 35 facing outward, and with breathable film 37 facing inward toward the dampness-inhibiting inner nonwoven web 50.

The nonwoven filament web 35 may be a spunbond web, a meltblown web, a bonded carded web, an air laid web, or any other filament-type nonwoven web which does not appreciably absorb aqueous fluid. Preferably, the nonwoven web 35 is made from one or more thermoplastic polymers. Suitable polymers include, without limitation, polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain, polyamides, and polyesters. Other suitable polymers include without limitation elastomers, for example polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly(ethylene-butylene)/polystyrene, poly (styrene/ethylene-butylene/styrene), and the like. Metallocene-catalyzed polyolefins are also useful, including those described in U.S. Pat. Nos. 5,571,619; 5,322,728; and 5,272,236, the disclosures of which are incorporated herein by reference.

Polymers made using metallocene catalysts have a very narrow molecular weight range. Polydispersity numbers (Mw/Mn) of below 4 and even below 2 are possible for metallocene-produced polymers. These polymers also have a controlled short chain branching distribution compared to otherwise similar Ziegler-Natta produced type polymers. It is also possible using a metallocene catalyst system to control the isotacticity of the polymer quite closely.

The nonwoven web 35 is preferably made of polyethylene, polypropylene, or a semi-crystalline propylene-ethylene copolymer. The web 35 is laminated to breathable film 37 using patterned thermal calender bonding, ultrasonic bonding, adhesive bonding, or the like. Preferably, the bonded regions will cover less than about 25%, more preferably less than about 20% of the interface between web 35 and film 37, so that the bonding does not impede breathability of the laminate 16. Preferably, the nonwoven web 35 is not creped.

Figure 3:
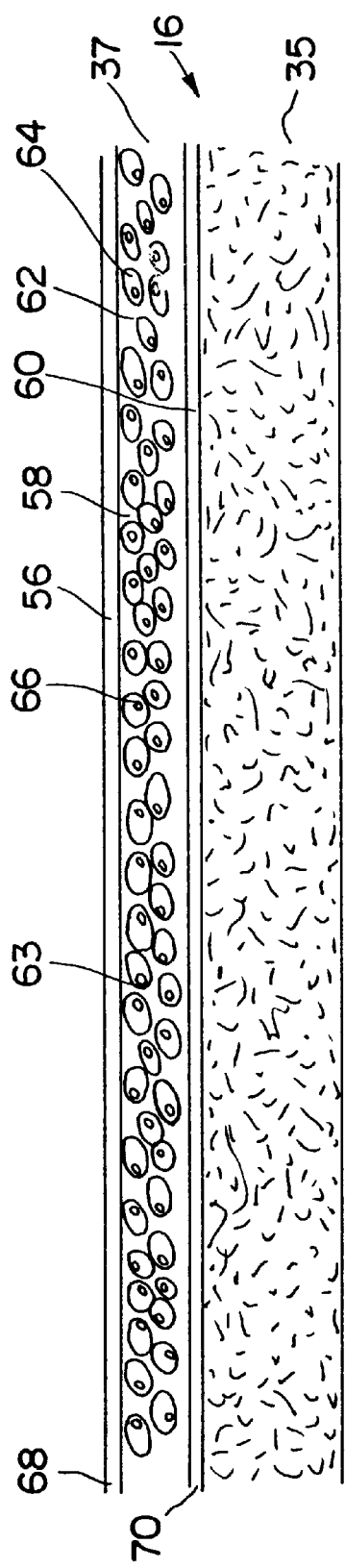
FIG. 3 is an expanded sectional view of one embodiment of the breathable outer cover material.

The breathable film 37 is illustrated in more detail in FIG. 3, which is an expanded sectional view of outer cover 16. In one embodiment, breathable film 37 includes at least one microporous layer 58. The microporous layer 58 can be formed using a variety of known technologies. Preferably, layer 58 includes a polymer matrix 62, a plurality of voids 64 within the matrix surrounded by relatively thin microporous membranes 63 defining tortuous paths, and one or more filler particles 66 in each void 64. The layer 58 is microporous and breathable, wherein the microporous membranes 63 between the voids readily permit molecular diffusion of water vapor from a first surface 68 to a second surface 70 of the film layer 58.

The polymer matrix 62 can be formed from any suitable film-forming thermoplastic polymer. Examples of suitable polymers include without limitation the thermoplastic polymers listed above, which can be used for the nonwoven web 35.

Polyolefins are preferred, and liner low density polyethylenes formed using a Ziegler-Natta or metallocene catalyst are most preferred.

The filler particles 66 can include any suitable inorganic or organic filler. The filler particles 66 are preferably small, in order to maximize vapor transmission through the voids. Generally, the filler particles should have a mean particle diameter of about 0.1–7.0 microns, preferably about 0.5–7.0 microns, most preferably about 0.8–2.0 microns. Suitable fillers include without limitation calcium carbonate, non-swellable clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin, mica, carbon, calcium oxide, magnesium oxide, aluminum hydroxide and polymer particles. Calcium carbonate is a presently preferred filler.

The filler particles 66 may be coated with a minor quantity (e.g. up to 2% by weight) of a fatty acid or other material to ease their dispersion in the polymer matrix. Suitable fatty acids include without limitation stearic acid, or a larger chain fatty acid such as behenic acid. The amount of filler particles 66 in the layer 52 should range from about 30–80% by weight of the layer 58, preferably about 40–70% by weight, most preferably about 50–65% by weight. Similarly, the polymer matrix 62 should constitute about 20–70% by weight of the layer 58, preferably about 30–60% by weight, more preferably about 35–50% by weight.

The polymer composition, filler content, filler particle size and degree of stretching are factors which help determine the breathability of the microporous film layer 58. Generally, the microporous film layer 58 will be less than about 50 microns thick, preferably less than about 30 microns thick, most preferably less than about 20 microns thick. The breathable film 37 may be uniaxially stretched to about 1.1–7.0 times its original length, preferably to about 1.5–6.0 times its original length, most preferably to about 2.5–5.0 times its original length. The film may alternatively be biaxially stretched using conventional techniques familiar to persons skilled in the art.

In the embodiment of FIG. 3, the microporous breathable film layer 58 is adjacent one or two relatively thin outer skin layers 56 and 60, in a two or three-layer film 37. The inclusion of one or two skin layers improves film process-ability and can also contribute heat seal properties to the breathable film 37. The breathable film 37 can be prepared by cast or blown film coextrusion of the layers, by extrusion coating, or by any conventional layering process. The polymers in the outer layers 56 and 60 can be the same or different than the polymers in the microporous layer 58. Preferably, the polymers in the outer layer or layers have a lower softening point than in the microporous layer 58, and contribute to the heat sealability of the film 37.

Also, the thickness and composition of the outer layers 56 and 60 should be selected so as not to substantially impair the moisture transmission through the breathable film 37. This way, the microporous layer 58 may determine the breathability of the entire film. To this end, the skin layers 56 and 60 each are generally less than about 10 microns thick, preferably less than about 5 microns thick, most preferably less than about 2.5 microns thick. Preferred skin layer polymers include ethylene vinyl acetates, propylene vinyl acetates, ethylene methyl acrylates, other vapor-permeable polymers, and blends of these with other polyolefins.

In accordance with the invention, a dampness-inhibiting nonwoven filament web 50 is disposed between the absorbent core 17 and the outer cover 16. The nonwoven web 50 may be a spunbond web, a meltblown web, a bonded carded web, an air laid web, or any other microfibrous nonwoven web. Preferably, the nonwoven web 50 is made of thermoplastic polymer fibers. The polymers used to make the nonwoven web include the polymers listed above for the breathable microporous film 37, and the nonwoven web 35. The nonwoven web 50 is preferably constructed of a polyolefin, more preferably a polyethylene or polypropylene homopolymer or copolymer. The nonwoven web 50 should have a basis weight of about 0.1–4.0 ounces per square yard (osy), preferably about 0.3–2.0 osy, more preferably about 0.4–1.0 osy. The nonwoven web 50 may also be a laminate of more than one nonwoven web layer. For example, web 50 may be a spunbond-meltblown-spunbond structure as disclosed in U.S. Pat. No. 4,041,203, issued to Brock et al. If the nonwoven web 50 includes more than one layer, then the basis weight is calculated based on the combined layers, to give values which represent the web 50 in its entirety.

The nonwoven web 50 is creped. Preferably, nonwoven web 50 is made of thermoplastic filaments. More preferably, the web 50 is a permanently creped thermoplastic nonwoven web having interfilament bonded areas which are bent or oriented permanently out-of-plane, unbonded areas between the bonded areas, and substantial filament looping in the unbonded areas.

If nonwoven web 50 includes more than one layer, one or more of the layers may be individually creped and then combined. For instance, in a spunbond-meltblown-spunbond nonwoven laminate, one or more of the spunbond and meltblown layers may be creped and then combined. Alternatively, the combined layers may be creped together. Multiple layers may be employed to provide density gradients or surface energy gradients in the nonwoven web 50.

The starting material used to make the web 50 is an uncreped thermoplastic nonwoven web 50 which can, for instance, be a thermoplastic spunbonded web or a thermoplastic meltblown web. In the preferred creping process, the nonwoven web is at least partially coated on one side with an adhesive, so that about 5–100% (preferably 10–70%) of the total surface area on one side is coated, and about 0–95% (preferably 30–90%) of the area is uncoated. The starting material for nonwoven web 50 also possesses interfilament bonding, in the form of a pattern called the "nonwoven web bond pattern," which is imparted during manufacture of the nonwoven web. The adhesive applied to the nonwoven web is concentrated to a greater extent in the interfilament-bonded areas, causing still greater interfilament bonding in those areas. The at least partially coated side of the thermoplastic nonwoven web is then placed against a creping surface, such as a creping drum, and is peelably bonded to the creping surface. The creping surface is preferably heated, and is moved (e.g., rotated) in a machine direction. As the creping surface moves, the leading edge of the nonwoven web bonded to the surface is creped off using a doctor blade.

The doctor blade penetrates the adhesive coating underneath the web and lifts the nonwoven web off the drum, resulting in permanent filament bending in the bonded areas corresponding to the nonwoven web bond pattern, and permanent looping of the filaments in the unbonded areas. Only one side of the web need be creped in this fashion to form a creped nonwoven web 50 suitable for use in the invention. Alternatively, both sides of the web may be creped by applying the adhesive on the second surface of the web as well as the first, adhering the second surface of the web to the same or a different creping surface, and creping the second side of the web from the creping surface using a doctor blade.

Figure 7:
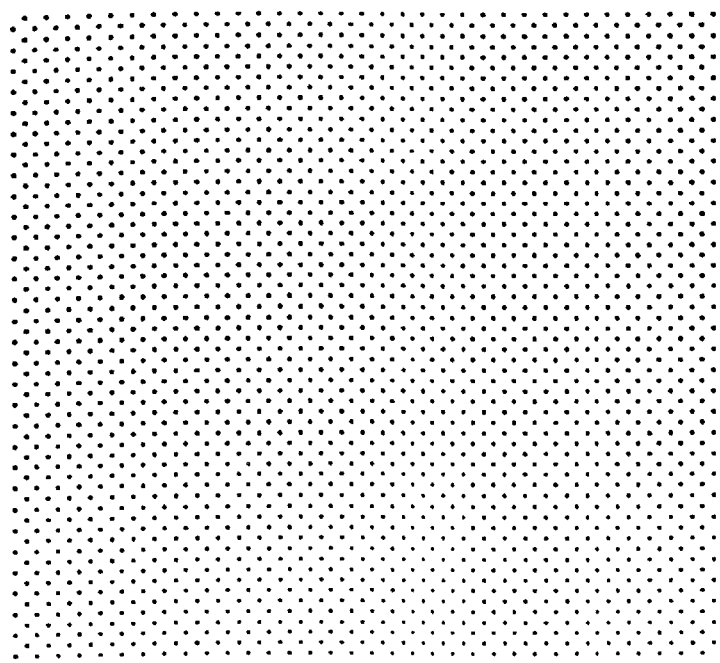
FIGS. 7–9 illustrate nonwoven web bonding patterns for the precursor nonwoven web.

Various nonwoven web bond patterns can be imparted during manufacture of the precursor web. A presently preferred nonwoven web bonding pattern is a regular point bond pattern referred to as the Hansen & Pennings or "HP" pattern, shown in FIG. 7. The HP pattern has a bond area of 19–32%, a bond density of 204 points/in$^2$, and a point height or depth of 0.030 in. This bond pattern results in the formation of regular fiber loops and excellent bulk.

Figure 8:
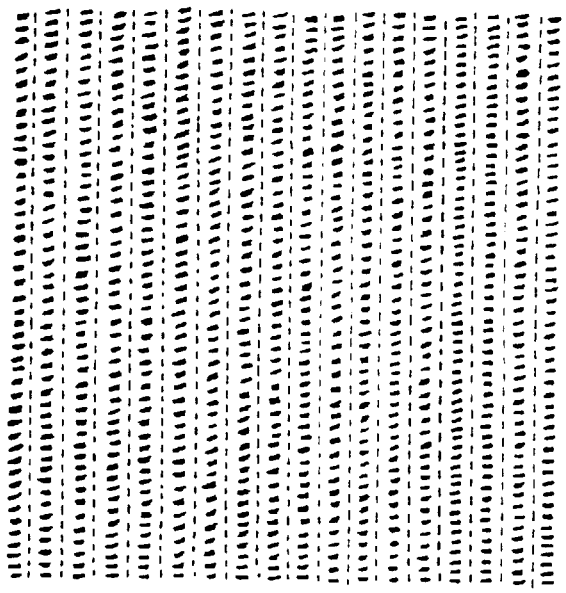

Another suitable nonwoven web bond pattern is the "rib knit" pattern shown in FIG. 8. The rib knit pattern is designed for a knitted fabric appearance. The pattern has a bond area of 10–20%, a bond density of 212 bond points/in$^2$, and a bond point height or depth of 0.044 in. This pattern provides creped nonwoven fabrics with excellent softness.

Figure 9:
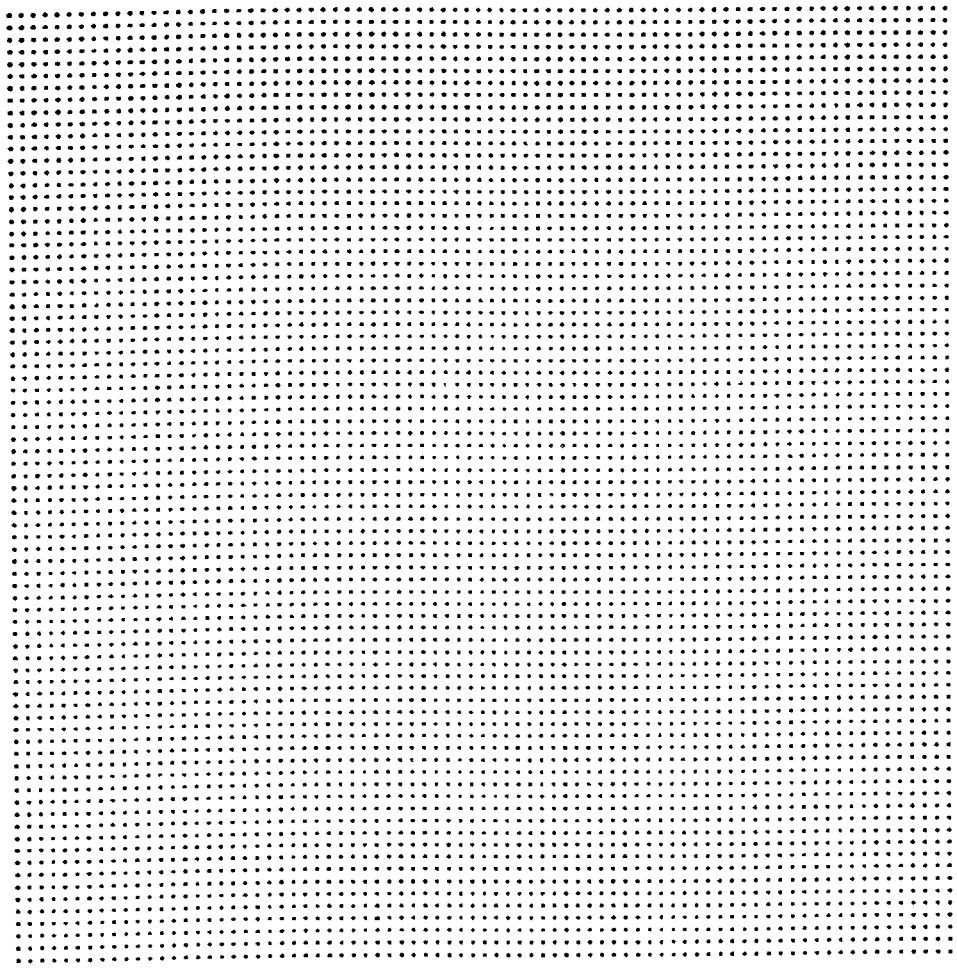

Another suitable nonwoven web bond pattern, characterized by elliptical-shaped point bonds, is the "wire weave" pattern shown in FIG. 9. The wire weave pattern has a bond area of 15–21%, a bond density of 302 point/in$^2$, and a bond point height or depth of 0.038 in. This pattern is designed to provide a nonwoven fabric with a woven look, and results in creped nonwoven fabrics having good softness, bulk, and fiber looping.

Figure 4:
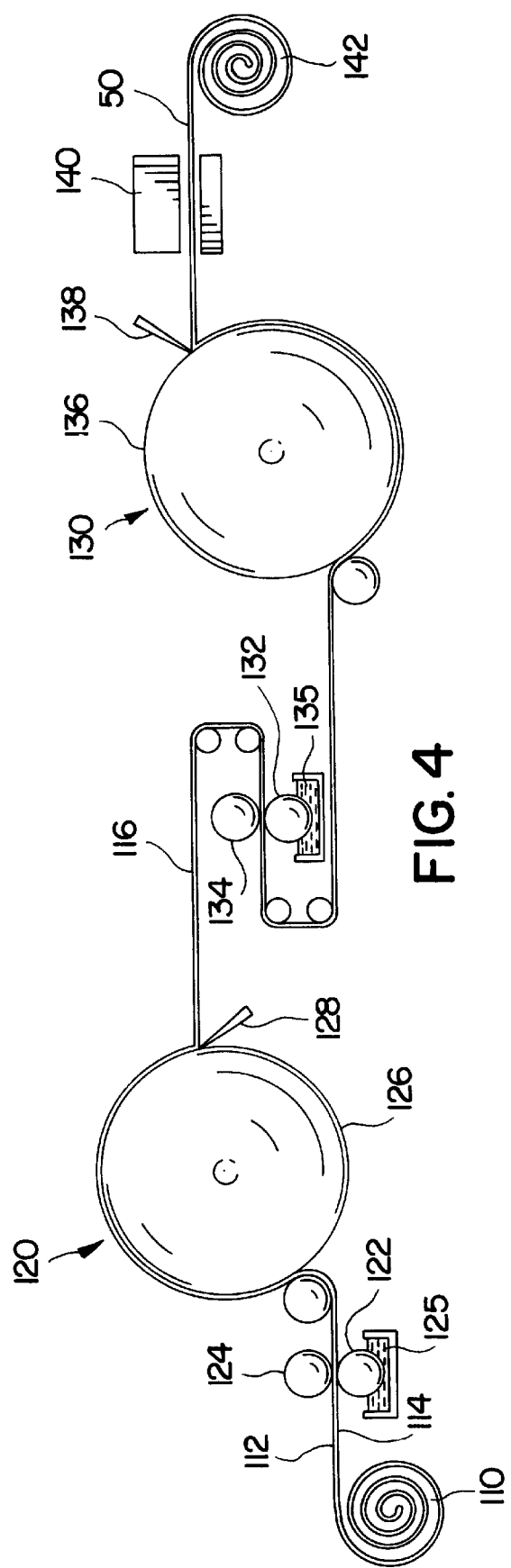
FIG. 4 schematically illustrates one process for making a creped nonwoven web useful in the invention.

FIG. 4 illustrates a process for preparing a creped nonwoven web 50 used in the invention. A preferred web 50 can be a creped spunbonded web, and can be creped on one or both sides. A precursor nonwoven web 112 is unwound from a supply roll 110. The nonwoven web 112 may be passed through a first creping station 120, a second creping station 130, or both. If it is desired to crepe the nonwoven web 112 on only one side, it may be passed through either the first creping station 120 or the second creping station 130, with one creping station or the other being bypassed. If it is desired to crepe the nonwoven web 112 on both sides, it may be passed through both creping stations.

A first side 114 of the web 112 may be creped using the first creping station 120. The creping station 120 includes first a printing station including a lower patterned or smooth printing roller 122, an upper smooth anvil roller 124, and a printing bath 125, and also includes a dryer roller 126 and associated creping blade 128.

The rollers 122 and 124 nip the web 112 and guide it forward. As the rollers 122 and 124 turn, the patterned or smooth printing roller 122 dips into bath 125 containing an adhesive material, and applies the adhesive material to the first side 114 of the web 112 in a partial coverage at a plurality of spaced apart locations, or in a total coverage. The adhesive-coated web 112 is then passed around drying drum 126 whereupon the adhesive-coated surface 114 becomes adhered to the roller 126. The first side 114 of the web 112 is then creped (i.e., lifted off the drum and bent) using doctor blade 128.

A second side 116 of the web 112 may be creped using the second creping station 130, regardless of whether or not the first creping station 120 has been bypassed. The second creping station 130 includes a second printing station including a lower patterned or smooth printing roller 132, an upper smooth anvil roller 134, and a printing bath 135, and also includes a dryer drum 136 and associated creping blade 138. The rollers 132 and 134 nip the web 112 and guide it forward. As the rollers 132 and 134 turn, the printing roller 132 dips into bath 135 containing adhesive material, and applies the adhesive to the second side 116 of the web 112 in a partial or total coverage. The adhesive-coated web 112 is then passed around drying roller 136 whereupon the adhesive-coated surface 116 becomes adhered to the roller 136. The second side 116 of the web 112 is then creped (i.e., lifted off the drum surface and bent) using doctor blade 138.

After creping, the creped nonwoven web 50 may be passed through a chilling station 140 and wound onto a storage roll 142. The level of creping is affected by the surface speed of the windup roll 142 relative to the surface speed of the creping drum 136, according to the equation presented above. The surface speed of the windup roll 142 is slower than the surface speed of the creping drum 136, and the difference between the two speeds affects the level of creping. The level of creping should generally be about 5–75%, preferably about 15–60%, most preferably about 25–50%.

A wide variety of adhesive bonding materials may be utilized to reinforce the fibers of the precursor web 112 at the locations of adhesive application, and to temporarily adhere the web 112 to the surface of the drum 126 and/or 136. Elastomeric adhesives (i.e., materials capable of at least 75% elongation without rupture) are especially suitable. Suitable materials include without limitation aqueous-based styrene butadiene adhesives, neoprene, polyvinyl chloride, vinyl copolymers, polyamides, and ethylene vinyl terpolymers. The presently preferred adhesive material is an acrylic polymer emulsion sold by the B.F. Goodrich Company under the trade name HYCAR®. The adhesive may be applied using the printing technique described above or may, alternatively, be applied by meltblowing, melt spraying, dripping, splattering, or any technique capable of forming a partial or total adhesive coverage on the thermoplastic nonwoven web 112.

The percent adhesive coverage of the web 112 generally affects the level of creping obtained. Generally the adhesive should cover about 5–100% of the web surface, preferably about 10–70% of the web surface, more preferably about 25–50% of the web surface. In the presently preferred embodiment, the web 112 is coated with adhesive and creped on only one side. The web 112 may be coated with adhesive and creped on both sides, however. The adhesive should also penetrate the nonwoven web 112 in the locations where the adhesive is applied. Generally, the adhesive should penetrate through about 10–50% of the nonwoven web thickness, although there may be greater or less adhesive penetration at some locations.

Figure 5:
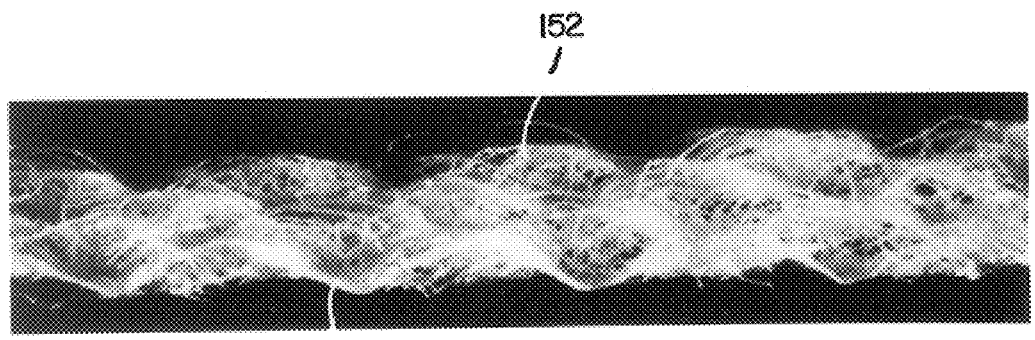
FIGS. 5 and 6 are photographs showing permanently creped nonwoven webs made according to the process of FIG. 4.
Figure 6:
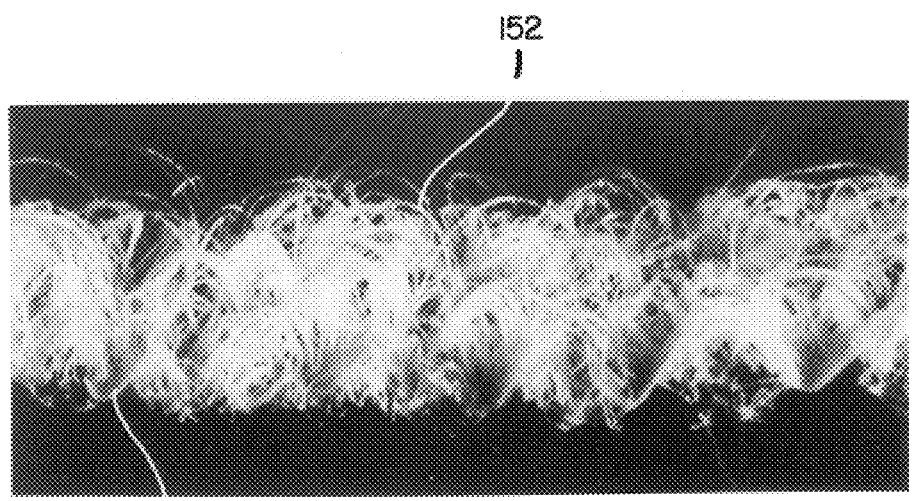

The resulting creped nonwoven web 50 has a controlled pattern creping which corresponds generally to the nonwoven web bond pattern. The adhesive applied to the web tends to concentrate more in the regions where interfilament bonding already exists, where the filament density is higher and less in the regions where the filaments are unbonded and spaced apart. Thus, when the web is creped, the amount of adhesive reinforcement in the interfilament-bonded regions (corresponding to the nonwoven web bond pattern) is sufficient to render the creping (i.e., out-of-plane bending) permanent in these regions. Looped filament regions tend to exist between the permanently creped regions, the looped regions existing where the filaments have not been bonded together. FIGS. 5 and 6 illustrate a spunbonded web creped according to the invention at creping percentages of 25% and 50%, respectively. As shown in FIGS. 5 and 6, each of the creped webs has creped nonwoven web bond regions 150 which are bent permanently out-of-plane due to the creping. Looped regions 152 corresponding to the unbonded, non-creped regions exist between the creped regions. The creped regions 150 include tightly bonded filament regions, while the looped regions 152 include loose filament regions. The individual filament loops terminate at both ends in the adhesive-reinforced regions, and are anchored in the adhesive-reinforced regions. As seen in FIGS. 5 and 6, the degree of looping increases substantially when the level of creping is increased from 25% to 50%. The completeness of the loops suggest that there is very little fiber breakage. The same spunbond web prior to creping has a substantially flat or planar configuration.

In one preferred embodiment, the creped nonwoven web is formed from a web composed totally or partially of hollow fibers, for example, hollow spunbond fibers or hollow meltblown fibers. Hollow nonwoven fibers, and processes for making them, are described in U.S. Pat. No. 5,439,626, issued to Bennett et al.; U.S. Pat. 5,656,372, issued to Gentile et al.; U.S. Pat. No. 4,284,594, issued to Joh et al.; and U.S. Pat. No. 4,288,494, issued to Porter et al., the disclosures of which are incorporated by reference. The hollow fibers tend to be structurally rigid, and readily maintain the out-of-plane bending imparted by the creping. Also, the hollow fibers contain additional air, which improves the insulative properties of the creped nonwoven web 50 in the absorbent article.

In another preferred embodiment, the creped nonwoven web 50 has a first hydrophobic side and a second hydrophilic side. In an absorbent article, the first hydrophobic side faces toward the outer cover and the second hydrophilic side faces toward the absorbent core. The hydrophobic surface facing the outer cover repels water and thus traps drier air at that interface, lowering the thermal conductivity at that location. The hydrophilic surface facing the absorbent core attracts water at that location.

The creped nonwoven web 50 having hydrophobic and hydrophilic sides may be formed by creping one side with a hydrophobic adhesive (as described above) and creping the other side with a hydrophilic adhesive. Alternatively, the web 50 may be formed by creping a first web layer with a hydrophobic adhesive, creping a second web layer with a hydrophilic adhesive, and combining the layers together. Other techniques may also be employed.

Examples of suitable hydrophilic adhesives includes without limitation a material sold under the trade name HYCAR® by the B.F. Goodrich Company. HYCAR® is an acrylic polymer emulsion containing a 20:1 weight ratio of a latex acrylic polymer and an additional surfactant. The additional surfactant is sold under the trade name AHCOVEL® by Imperial Chemical Industries, Ltd. and is composed of a 55:45 mixture of hydrogenated ethoxylated castor oil and sorbitan monooleate. The effective wetting agent is the castor oil derivative.

Other hydrophilic latex-based adhesives may also be used including, for example, other acrylic based latices. One such acrylic-based latex is sold by Air Products Co. under the trade name AIRFLEX® A-105. Hydrophilic styrene butadiene rubber-based adhesives may also be employed. Other surfactants may also be employed in combination with the adhesives, which surfactants are useful as wetting or rewetting agents. Another example of a suitable surfactant is TRITON® X-100, sold by the Union Carbide Corp.

The above-described adhesives can be described generally as latex-based adhesives which are rendered hydrophilic by the inclusion of hydrophilic surfactants. As an alternative to employing a surfactant, the adhesive itself may be composed of one or more hydrophilic polymer materials. An example of a hydrophilic polymer-based adhesive is AIR-VOL® 523, sold by Air Products Co. This adhesive is based on polyvinyl alcohol having a medium molecular weight and about 88% hydrolysis. In other embodiments of the adhesive, polyvinyl alcohol may be combined with sorbitol at weight ranges of about 70–100% polyvinyl alcohol and 0–30% sorbitol.

Other hydrophilic polymer-based adhesives include without limitation adhesives based on natural gums (e.g., guar gum and pectin), starch and starch derivatives, and cellulose derivatives (e.g., methylcellulose, carboxymethyl cellulose, and hydroxyalkyl celluloses). Hydrophilic adhesives may be applied using the printing technique described above or, alternatively, by melt blowing, melt spraying, dripping, splattering, or any technique capable of producing a partial or total adhesive coverage on the inner side of the creped web 50.

Test Procedure For Water Vapor Transmission Rate (WVTR)

The following procedure is described for testing of the water vapor transmission rate (WVTR) for breathable films and laminates. The WVTR is measured in a manner similar to ASTM Standard Test Method for Water Vapor Transmission of Materials, Designation E-96-80 as follows. For the purposes of the present invention, 3 inch diameter (76 mm) circular samples are cut from the test material and from a control material, CELGUARD®2500 (Hoechst Celanese Corporation). CELGUARD®2500 is a 0.0025 cm thick film composed of microporous polypropylene. Two or three samples are prepared for each material.

The cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred millimeters of distilled water is poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.).

The cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred milliliters of distilled water is poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.).

The oven is a constant temperature oven with external air through it to prevent water vapor accumulation inside. A suitable forced air oven is, for example, a BLUE M POWER-O-MATIC 60® oven distributed by Blue M Electric Co. of Blue Island, Ill. After 24 hours, the cups are removed from the oven and weighed. The preliminary test WVTR value is calculated as follows:

Test WVTR=[(grams weight loss over 24 hours)×7571]÷24

The relative humidity within the oven is not specifically controlled. Under predetermined set conditions of 100° F. and ambient relative humidity, the WVTR for CELGUARD®2500 has been determined to be 5000 g/m$^2$/24 hours. Accordingly, CELGUARD®2500 is run as a control sample with each test and the resulting values are corrected in accord with the variation of the control relative to its known WVTR.

We claim:

1. An absorbent article, comprising:
   a liquid-permeable top layer;
   an absorbent core layer;
   an inner nonwoven fibrous web; and
   a breathable, outer cover having a WVTR of at least about 300 grams/m²–24 hours;
   the breathable, liquid-impermeable outer cover positioned such that the inner nonwoven fibrous web is between the absorbent core layer and outer cover;
   wherein the inner nonwoven fibrous web has been creped to cause regions of out-of-plane bending.

2. The absorbent article of claim 1, wherein the inner nonwoven fibrous web is at least partially covered with an adhesive, and has creped interfilament-bonded regions alternating with regions of no interfilament bonding;
   the inner nonwoven fibrous web having a nonwoven web bond pattern which effects the interfilament-bonded regions, and controlled pattern creping which corresponds generally to the nonwoven web bond pattern.

3. The absorbent article of claim 2, wherein the interfilament-bonded regions are creped so as to exhibit permanent out-of-plane bending, and the regions of no interfilament bonding include a multiplicity of loops which terminate in the interfilament-bonded regions.

4. The absorbent article of claim 1, wherein the inner nonwoven fibrous web has a level of creping of about 5–75%.

5. The absorbent article of claim 1, wherein the inner nonwoven fibrous web has a level of creping of about 15–60%.

6. The absorbent article of claim 1, wherein the inner nonwoven fibrous web has a level of creping of about 25–50%.

7. The absorbent article of claim 1, wherein the inner nonwoven web has a basis weight of about 0.1–4.0 osy.

8. The absorbent article of claim 1, wherein the inner nonwoven web has a basis weight of about 0.3–2.0 osy.

9. The absorbent article of claim 1, wherein the inner nonwoven web has a basis weight of about 0.4–1.0 osy.

10. The absorbent article of claim 1, wherein the inner nonwoven web comprises a polymer selected from the group consisting of polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, flexible polyolefins including propylene-based polymers having both atactic and isotactic propylene groups in the main polypropylene chain, polyamides, polyesters, and combinations thereof.

11. The absorbent article of claim 1, wherein the inner nonwoven web comprises a polymer selected from the group consisting of polyurethanes, copolyether esters, polyamide polyether block copolymers, ethylene vinyl acetate copolymers, block copolymers having the general formula A-B-A' or A-B such as copoly (styrene/ethylene-butylene), styrene-poly (ethylene-propylene)-styrene, styrene-poly (ethylene-butylene)-styrene, polystyrene/poly(ethylene-butylene)/polystyrene, poly (styrene/ethylene-butylene/styrene), and combinations thereof.

12. The absorbent article of claim 1, wherein the inner nonwoven web comprises a polyolefin.

13. The absorbent article of claim 1, wherein the inner nonwoven web comprises a metallocene-catalyzed polyolefin.

14. The absorbent article of claim 1, wherein the inner nonwoven web comprises a spunbonded web.

15. The absorbent article of claim 1, wherein the inner nonwoven web comprises a meltblown web.

16. The absorbent article of claim 2, wherein the adhesive comprises an elastomeric adhesive.

17. The absorbent article of claim 2, wherein the adhesive comprises a material selected from the group consisting of styrene butadiene adhesives, neoprene, polyvinyl chloride, vinyl copolymers, polyamides, ethylene vinyl terpolymers, and combinations thereof.

18. The absorbent article of claim 1, wherein the breathable outer cover comprises at least a breathable film and an outer fibrous nonwoven web.

19. The absorbent article of claim 18, wherein the breathable film is between the outer nonwoven fibrous web and the inner nonwoven fibrous web.

20. The absorbent article of claim 1, wherein the inner nonwoven web comprises a first hydrophobic surface and a second hydrophilic surface.

21. The absorbent article of claim 20, wherein the inner nonwoven web comprises a plurality of layers.

22. The absorbent article of claim 1, comprising a diaper.

23. The absorbent article of claim 1, comprising a training pant.

24. The absorbent article of claim 1, comprising an adult incontinence garment.

25. The absorbent article of claim 1, comprising swim wear.

26. The absorbent article of claim 1, comprising a medical absorbent product.

27. An absorbent article, comprising:
   a liquid-permeable top layer;
   an absorbent core layer;
   a dampness-inhibiting inner nonwoven fibrous web having a level of creping of about 5–75%; and
   a breathable, liquid-impermeable outer cover having a WVTR of at least about 300 grams/m²–24 hours;
   the breathable outer cover positioned such that the inner nonwoven fibrous web is between the absorbent core layer and breathable outer cover;
   the outer cover including a breathable film facing the inner nonwoven fibrous web and an outer nonwoven fibrous web facing away from the inner nonwoven fibrous web.

28. The absorbent article of claim 27, wherein the inner nonwoven fibrous web has a basis weight of about 0.1–4.0 osy.

29. The absorbent article of claim 27, wherein the inner nonwoven fibrous web has a basis weight of about 0.3–2.0 osy.

30. The absorbent article of claim 27, wherein the inner nonwoven fibrous web has a basis weight of about 0.4–1.0 osy.

31. The absorbent article of claim 27, wherein the inner nonwoven fibrous web comprises a spunbond web.

32. The absorbent article of claim 27, wherein the inner nonwoven fibrous web comprises a meltblown web.

33. The absorbent article of claim 27, wherein the inner nonwoven fibrous web comprises a bonded carded web.

34. The absorbent article of claim 27, wherein the inner nonwoven fibrous web comprises an air laid web.

35. The absorbent article of claim 27, wherein the inner nonwoven fibrous web comprises hollow fibers.

36. The absorbent article of claim 27, wherein the inner nonwoven fibrous web has a level of creping of about 15–60%.

37. The absorbent article of claim 27, wherein the inner nonwoven fibrous web has a level of creping of about 25–50%.

38. An absorbent article, comprising:

a liquid-permeable top layer;

an absorbent core layer;

a dampness-inhibiting inner nonwoven fibrous web having a basis weight of about 0.1–4.0 osy and a level of creping of about 5–75%;

a breathable, liquid-impermeable outer cover including a breathable microporous film facing the inner nonwoven fibrous web, and an outer nonwoven fibrous web facing away from the inner nonwoven fibrous web;

wherein the inner nonwoven fibrous web comprises hollow fibers and is positioned between the absorbent core layer and the breathable outer cover.

39. The absorbent article of claim 38, comprising a diaper.

40. The absorbent article of claim 38, comprising a training pant.

41. The absorbent article of claim 38, comprising an adult incontinence garment.

42. The absorbent article of claim 38, comprising swim wear.

43. The absorbent article of claim 38, comprising a medical absorbent product.

* * * * *